US009308164B2

(12) United States Patent
Srinivasan et al.

(10) Patent No.: US 9,308,164 B2
(45) Date of Patent: Apr. 12, 2016

(54) HYOSCYAMINE DOSAGE FORM

(75) Inventors: Viswanathan Srinivasan, The Woodlands, TX (US); Ralph Brown, Southlake, TX (US); David Brown, Colleyville, TX (US); Himanshu Patel, North Richland Hills, TX (US); Juan Carlos Menendez, Bedford, TX (US); Somphet Peter Suphasawud, Fort Worth, TX (US)

(73) Assignee: Sovereign Pharmaceuticals, LLC, Fort Worth, TX (US)

( * ) Notice: Subject to any disclaimer, the term of this patent is extended or adjusted under 35 U.S.C. 154(b) by 3618 days.

(21) Appl. No.: 10/879,506

(22) Filed: Jun. 30, 2004

(65) Prior Publication Data

US 2007/0202167 A1 Aug. 30, 2007

(51) Int. Cl.
*A61K 31/46* (2006.01)
*A61K 9/00* (2006.01)
*A61K 9/24* (2006.01)

(52) U.S. Cl.
CPC .............. *A61K 9/0095* (2013.01); *A61K 9/209* (2013.01); *A61K 31/46* (2013.01)

(58) Field of Classification Search
None
See application file for complete search history.

(56) References Cited

U.S. PATENT DOCUMENTS

| | | | | |
|---|---|---|---|---|
| 2,793,979 A * | 5/1957 | Svedres | .......................... | 424/470 |
| 2,951,792 A * | 9/1960 | Swintosky | ..................... | 424/472 |
| 3,078,216 A * | 2/1963 | Greif | .............................. | 424/498 |
| 3,400,197 A * | 9/1968 | Lippmann | ..................... | 424/469 |
| 3,865,933 A * | 2/1975 | Mudge | ........................... | 424/677 |
| 4,443,428 A | 4/1984 | Oshlack et al. | | |
| 4,861,598 A * | 8/1989 | Oshlack | ........................ | 424/468 |
| 4,996,047 A * | 2/1991 | Kelleher et al. | ............... | 424/486 |
| 5,204,116 A | 4/1993 | Edgren et al. | | |
| 5,213,808 A | 5/1993 | Bar-Shalom et al. | | |
| 5,271,946 A * | 12/1993 | Hettche | ......................... | 424/490 |
| 5,338,550 A | 8/1994 | Edgren et al. | | |
| 5,378,474 A | 1/1995 | Morella et al. | | |
| 5,445,829 A * | 8/1995 | Paradissis et al. | ............ | 424/480 |
| 5,508,043 A | 4/1996 | Krishnamurthy | | |
| 5,558,879 A | 9/1996 | Chen et al. | | |
| 5,595,758 A * | 1/1997 | Adusumilli et al. | .......... | 424/456 |
| 5,738,874 A * | 4/1998 | Conte et al. | .................... | 424/472 |
| 5,811,126 A | 9/1998 | Krishnamurthy | | |
| 5,869,097 A | 2/1999 | Wong et al. | | |
| 6,114,347 A | 9/2000 | Hille et al. | | |
| 6,183,778 B1 | 2/2001 | Conte et al. | | |
| 6,419,954 B1 | 7/2002 | Chu et al. | | |
| 6,419,960 B1 * | 7/2002 | Krishnamurthy et al. | .... | 424/490 |
| 6,465,460 B1 * | 10/2002 | Hundley et al. | ............... | 514/242 |
| 6,699,502 B1 * | 3/2004 | Fanara et al. | .................. | 424/484 |
| 2003/0049318 A1 | 3/2003 | Davis et al. | | |
| 2003/0099711 A1 * | 5/2003 | Meadows et al. | .............. | 424/474 |
| 2004/0018233 A1 * | 1/2004 | Davis et al. | .................... | 424/468 |
| 2004/0224020 A1 * | 11/2004 | Schoenhard | ................... | 424/471 |
| 2005/0181050 A1 * | 8/2005 | Hirsh et al. | .................... | 424/469 |

OTHER PUBLICATIONS hyoscyamine_sulfate_drugs.com_NPL.pdf, from: http://www.drugs.com/ppa/hyoscyamine-sulfate.html.*
Muhtadi, Farid J.; Hyoscyamine; 1994; Academic Press; Analytical Profiles of Drug Substances and Excipients vol. 23, pp. 153-228 (Reference Supplied in Office action Dated May 30, 2008).*
Sinko, Patrick J.; "Martin's Physical Pharmacy and Pharmaceutical Sciences", 5th ed., 2005; Lippincott Williams & Wilkins; Chapters 13 and 14, pp. 337-396.*
Mathiowitz, Edith; "Controlled Drug Delivery", John Wiley & Sons; pp. 341-347 and 349-364.*
Sweetman, Sean C.; "Martindale: The Complete Drug reference", 2002, Pharmaceutical Press, pp. 459-475, 1082-1102 and 1322-1330.*
Product information sheet for "AMBERLITE™ IRP69", 2006, Rohm and Hass Company; pp. 1-4.*
Wang, Wenping; et al.; "Pharmacometrics: The Formulation of the Principle of Superposition in the Presence of Non-Compliance and Its Applications in Multiple Dose Pharmaceuticals", 1998, Plenum Publishing, Journal of Pharmacokinetics and Biopharmaceutics, vol. 26, No. 4, pp. 457-469.*
Physicians Desk Reference, entry for "Donnatal Extentabs™" Retrieved from <http://www.thomsonhc.com> on May 13, 2008, pp. 1-5.*
Muhtadi, Farid, J., Analytical Profiles of Drug Substances and Excipients vol. 23: Hyoscyamine, 1994, Academic Press, pp. 153-228.*
Browne, Thomas; "Therapeutic Effects of Hyoscyamine", 1882, British Medical Journal, pp. 1030-1031.*
Ansel, Howard C. et al.; "Pharmaceutical Dosage Forms and Drug Delivery Systems", 7th ed., 1999, Lippincott Williams & Wilkins, Chapters 1-5, 7, 8, 12 and 13; pp. 1-163, 179-228 and 296-396.*
Troy, David B. editor; "Remington: The Science and Practice of Pharmacy", 21st ed., May 2005; Lippincott Williams & Wilkins, Chapters 47 and 73; pp. 939-964 and 1405-1410.*
Serels, Scott et al.; "Prospective Study Comparing Hyoscyamine, Doxazosin, and Combination Therapy for the Treatment of Urgency and Frequency in Women", 1998, Wiley-Liss, Inc.; Neurourology and Urodynamics, vol. 17, pp. 31-36.*

* cited by examiner

*Primary Examiner* — Suzanne Ziska
*Assistant Examiner* — Ivan Greene
(74) *Attorney, Agent, or Firm* — Abel Law Group, LLP

(57) ABSTRACT

A pharmaceutical dosage form which comprises two or more different hyoscyamine formulations, at least one of the formulations being an immediate release hyoscyamine formulation and at least one other one being a controlled release hyoscyamine formulation. This abstract is neither intended to define the invention disclosed in this specification nor intended to limit the scope of the invention in any way.

51 Claims, No Drawings

HYOSCYAMINE DOSAGE FORM

BACKGROUND OF THE INVENTION

1. Field of the Invention

The present invention relates to a pharmaceutical dosage form which contains hyoscyamine and/or a pharmaceutically acceptable salt thereof in at least two different formulations with different release profiles. The present invention also relates to a process for manufacturing the dosage form and to methods for alleviating or treating conditions which can be alleviated by hyoscyamine.

2. Discussion of Background Information

Hyoscyamine has actions similar to atropine but is more potent in both its central and peripheral effects. It inhibits gastrointestinal propulsive motility and decreases gastric acid secretions. It also controls excessive pharyngeal, tracheal, and bronchial secretions. Physicians rely on its ability to relieve intestinal hypermotility by prescribing hyoscyamine, usually in the form of hyoscyamine sulfate, for the relief of diarrhea and accompanying intestinal and stomach cramping. It is also used by physicians in the treatment of diverticulitis. By reducing acid secretions in the stomach, hyoscyamine is also useful in the treatment of gastric ulcers. It can also be used to relieve visceral spasm and hypermotility in cystitis pylorospasm and associated abdominal cramps. In combination with appropriate analgesics, hyoscyamine is also used for relief of biliary and renal colic and as a drying agent in the relief of symptoms of acute rhinitis. Hyoscyamine is also used in the treatment of irritable bowel syndrome, urinary incontinence and acute enterocolitis and related gastrointestinal disorders. Hyoscyamine further is indicated for the amelioration of allergic reactions, the treatment of motion sickness and the prevention and control of nausea and vomiting associated with certain types of anesthesia and surgery.

Once absorbed, hyoscyamine disappears rapidly from the blood and maintains therapeutic levels for approximately 3.5 hours. The majority of hyoscyamine is excreted in the urine unchanged within the first 12 hours.

Patients suffering from excessive gastrointestinal propulsive motility, excessive gastric acid secretions, excessive pharyngeal, tracheal, and bronchial secretions and symptoms of intestinal hypermotility such as diarrhea, intestinal and stomach cramping, diverticulitis, gastric ulcers, visceral spasm, cystitis pylorospasm, biliary and renal colic, irritable bowel syndrome, urinary incontinence, acute enterocolitis and related gastrointestinal disorders as well as patients suffering from acute rhinitis and related allergic symptoms and patients suffering motion sickness and nausea and vomiting may endure periods of 6 hours per day without adequate control of their symptoms if they are prescribed conventional hyoscyamine sulfate tablets or liquids. Dosages of these products are prescribed at intervals of 4 hours. With such dosages, the therapeutic level of the product is reached in about 30 minutes to one hour after ingestion and falls below therapeutic levels 30 minutes to over an hour before the next dose is taken. Even if patients ingest sustained-release or timed-release tablets, they must endure as many as 4 hours per day without adequate control of their symptoms, due to the slow release of the timed-release or sustained release product from the matrix in which hyoscyamine sulfate is embedded.

SUMMARY OF THE INVENTION

The present invention provides a pharmaceutical dosage form which comprises hyoscyamine and/or a pharmaceutically acceptable salt thereof. This dosage form comprises two or more (different) hyoscyamine formulations. At least one of the formulations is an immediate release formulation and at least one other one is a controlled release formulation.

In one aspect, the dosage form may comprise two hyoscyamine formulations.

In another aspect, the dosage form and/or the immediate release formulation thereof may be capable of providing a hyoscyamine plasma concentration within the therapeutic range within not more than about 1.5 hours, e.g., within not more than about 1 hour, or within not more than 45 minutes, following the ingestion of the dosage form.

In yet another aspect, the dosage form may be capable of providing a hyoscyamine plasma concentration within the therapeutic range for a period of at least about 6 hours, e.g., at least about 8 hours, at least about 10 hours, or at least about 12 hours.

In a still further aspect of the dosage form, the one or more controlled release formulations thereof may be capable of providing a hyoscyamine plasma concentration within the therapeutic range for a period of at least about 4 hours, e.g., at least about 5 hours, at least about 6 hours, at least about 8 hours, or at least about 12 hours.

In another aspect, the dosage form may comprise hyoscyamine sulfate.

In another aspect, the dosage form may comprise hyoscyamine and/or a pharmaceutically acceptable salt thereof in a total amount of from about 0.01 mg (e.g., about 0.03 mg) to about 5 mg, expressed as hyoscyamine free base (the same applies to all amounts recited herein and in the appended claims, unless indicated otherwise). For example, the dosage form may comprise hyoscyamine and/or a pharmaceutically acceptable salt thereof in a total amount of at least about 0.1 mg, e.g., at least about 0.25 mg and/or in a total amount of not more than about 3 mg, or not more than about 2 mg.

In yet another aspect of the dosage form, the immediate release formulation may comprise hyoscyamine and/or a pharmaceutically acceptable salt thereof in an amount of not more than about 0.15 mg and/or the at least one controlled release formulation may comprise hyoscyamine and/or a pharmaceutically acceptable salt thereof in an amount of at least about 0.15 mg.

The present invention also provides a pharmaceutical dosage form which comprises hyoscyamine and/or a pharmaceutically acceptable salt thereof, which dosage form comprises at least two hyoscyamine formulations which exhibit different release profiles of hyoscyamine (and/or a pharmaceutically acceptable salt thereof). The dosage form is capable of providing a hyoscyamine plasma concentration within a therapeutic range for a period of at least about 4 hours.

In one aspect, this dosage form may be capable of providing a hyoscyamine plasma concentration within the therapeutic range within not more than about 1 hour following the ingestion of the dosage form.

In another aspect, the dosage form may be capable of providing a hyoscyamine plasma concentration within the therapeutic range for a period of at least about 6 hours.

In yet another aspect, the dosage form may comprise at least one immediate release hyoscyamine formulation and at least one controlled release hyoscyamine formulation. By way of non-limiting example, the at least one immediate release formulation may be capable of providing a hyoscyamine plasma concentration within the therapeutic range for a first period and the at least one controlled release formulation may be capable of providing a hyoscyamine plasma concentration within the therapeutic range for a second period. The dosage form may be capable of providing a hyoscyamine plasma concentration within the therapeutic range for a period which is longer than the first and second periods together. In another aspect, the at least one immediate release formulation may be capable of releasing the at least one of hyoscyamine and a pharmaceutically acceptable salt thereof for a first period and the at least one controlled release formulation may be capable of releasing the at least one of hyoscyamine and a pharmaceutically acceptable salt thereof for a second period, and the first and second periods may overlap to provide a hyoscyamine plasma concentration within the therapeutic range during a period within which neither the immediate release formulation by itself nor the controlled release formulation by itself would be capable of providing a hyoscyamine plasma concentration within the therapeutic range.

In yet another aspect of the dosage form, the dosage form may comprise hyoscyamine sulfate.

In another aspect, the dosage form may comprise hyoscyamine and/or a pharmaceutically acceptable salt thereof in a total amount of from about 0.03 mg to about 5 mg.

The present invention also provides a pharmaceutical dosage form which comprises hyoscyamine and/or a pharmaceutically acceptable salt thereof and which is capable of providing a hyoscyamine plasma concentration within the therapeutic range within a period of not more than about 1 hour following the ingestion of the dosage form and is capable of maintaining a hyoscyamine plasma concentration within the therapeutic range for at least about 4 hours.

In one aspect, the dosage form may be capable of maintaining a hyoscyamine plasma concentration within the therapeutic range for at least about 5 hours, e.g., for at least about 7 hours, and/or it may be capable of providing a hyoscyamine plasma concentration within the therapeutic range within a period of not more than about 0.75 hours.

In another aspect, the dosage form may comprise a tablet, for example, a tablet which comprises at least two layers such as, e.g., a bi-layered tablet.

In yet another aspect, the tablet may comprise a matrix which comprises an immediate release formulation and has dispersed therein particles which comprise at least one controlled release formulation.

In a still further aspect, the dosage form may comprise at least two kinds of particles, at least one kind of particles comprising an immediate release formulation and at least one other kind of particles comprising at least one controlled release formulation. For example, said particles may be combined in a capsule.

In yet another aspect, the dosage form may comprise a core which comprises the at least one controlled release formulation and a coating which surrounds the core at least partially and comprises an immediate release formulation.

In another aspect, the dosage form may comprise a solution or a suspension.

The present invention also provides a bi-layered hyoscyamine tablet. This tablet comprises a first layer which comprises a first formulation comprising hyoscyamine and/or a pharmaceutically acceptable salt thereof, and a second layer which comprises a second formulation comprising hyoscyamine and/or a pharmaceutically acceptable salt thereof. The second layer exhibits a release profile which is different from the release profile of the first layer.

In one aspect of this tablet, the first formulation may be an immediate release formulation and/or the second formulation may be a controlled release formulation.

In another aspect, the first formulation may be capable of providing a hyoscyamine plasma concentration within the therapeutic range within not more than about 1 hour following the ingestion of the tablet and/or the second formulation may be capable of providing a hyoscyamine plasma concentration within the therapeutic range for a period of at least about 3 hours.

In yet another aspect, both of the first and the second formulation may comprise hyoscyamine sulfate.

In a still further aspect of the tablet, the first layer and/or the second layer may comprise a pharmaceutically active ingredient which is different from hyoscyamine and a pharmaceutically acceptable salt thereof.

In yet another aspect of the bi-layered tablet, the first layer thereof may comprise from about 0.01 to about 1 mg of hyoscyamine sulfate and/or the second layer may comprise from about 0.1 to about 5 mg of hyoscyamine sulfate.

In another aspect, the tablet may comprise a total of from about 0.2 to about 3 mg of hyoscyamine sulfate.

In another aspect, the tablet may be capable of providing a hyoscyamine plasma concentration within the therapeutic range for at least about 6 hours, e.g., for at least about 10 hours.

The present invention further provides a multi-layered hyoscyamine tablet which comprises at least a first layer and a second layer. The first layer is an immediate release layer which comprises hyoscyamine and/or a pharmaceutically acceptable salt thereof, and the second layer is a controlled release layer which comprises hyoscyamine and/or a pharmaceutically acceptable salt thereof.

In one aspect, the tablet may be capable of providing a hyoscyamine plasma concentration within the therapeutic range within not more than about one hour following the ingestion of the tablet, and/or the tablet may be capable of maintaining a hyoscyamine plasma concentration within the therapeutic range for at least about 6 hours, e.g., for at least about 8 hours.

In another aspect, the tablet may comprise hyoscyamine sulfate.

In yet another aspect, the tablet may comprise at least one pharmaceutically active ingredient which is different from hyoscyamine and a pharmaceutically acceptable salt thereof.

In a still further aspect of the tablet, the layers may be discrete zones which are arranged adjacent to each other, or the second layer may be at least partially surrounded by the first layer.

The present invention also provides a liquid dosage form which comprises (a) hyoscyamine and/or a pharmaceutically acceptable salt thereof in an immediate release form and (b) hyoscyamine and/or a pharmaceutically acceptable salt thereof in a controlled release form.

In one aspect, this liquid dosage form may comprise a suspension.

In another aspect, the controlled release form may comprise a complex of hyoscyamine and/or a pharmaceutically acceptable salt thereof with a complexing agent. By way of non-limiting example, the complexing agent may comprise an ion-exchange resin e.g., sodium polystyrene sulfonate.

In yet another aspect, the liquid dosage form may comprise particles of a complex of at least one of hyoscyamine and a pharmaceutically acceptable salt thereof with an ion-exchange resin, which particles are provided, at least in part, with a controlled release coating. This controlled release coating may, for example, comprise an organic polymer such as, e.g., a methacrylate polymer.

The present invention further provides a method of alleviating or treating a condition which can be alleviated or treated by administering hyoscyamine. This method comprises the administration of any of the above-recited pharmaceutical dosage forms, including the various aspects thereof, to a subject in need thereof.

In one aspect, the conditions which can be alleviated or treated by administering hyoscyamine may comprise one or more of the following: gastrointestinal propulsive hypermotility, excessive gastric acid secretions, excessive pharyngeal, tracheal, and bronchial secretions, intestinal hypermotility, diarrhea and accompanying intestinal and stomach cramping, diverticulitis, symptoms of gastric ulcers, visceral spasm, hypermotility, cystitis pylorospasm and associated abdominal cramps, biliary and renal colic, symptoms of acute rhinitis, irritable bowel syndrome, urinary incontinence, acute enterocolitis and related gastrointestinal disorders, allergic reactions, motion sickness, nausea and vomiting.

In another aspect of the method, the dosage form may be administered not more than about three times per day, preferably, not more than about twice per day.

The present invention also provides a process for making a pharmaceutical dosage form recited above. This method comprises providing an immediate release formulation which comprises hyoscyamine and/or a pharmaceutically acceptable salt thereof and a controlled release formulation which comprises hyoscyamine and/or a pharmaceutically acceptable salt thereof and combining these formulations, e.g., by using a tablet press.

The present invention also provides any of the above-recited dosage forms, including the various aspects thereof, in association with instructions to administer the dosage form three or fewer times per day, e.g., once or twice per day.

The pharmaceutical dosage forms which constitute one aspect of the present invention include a dosage form which comprises hyoscyamine and/or a pharmaceutically acceptable salt thereof, and comprises two or more different hyoscyamine formulations, i.e., at least one immediate release formulation and at least one controlled release formulation.

The term "pharmaceutically acceptable salt" as used herein and in the appended claims refers to those salts of hyoscyamine that are not substantially toxic at the dosage administered to achieve the desired effect and do not independently possess significant pharmacological activity. The salts included within the scope of this term are pharmaceutically acceptable acid addition salts of a suitable inorganic or organic acid. Non-limiting examples of suitable inorganic acids are, for example, hydrochloric, hydrobromic, sulfuric and phosphoric acids. Non-limiting examples of suitable organic acids include carboxylic acids, such as acetic, propionic, tannic, glycolic, lactic, pyruvic, malonic, succinic, fumaric, malic, tartaric, citric, cyclamic, ascorbic, maleic, hydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acids, as well as sulfonic acids such as, e.g., methanesulfonic, ethanesulfonic, and β-hydroxyethanesulfonic acids. A particularly preferred pharmaceutically acceptable salt of hyoscyamine is the sulfate. However, the present invention is not limited to hyoscyamine sulfate and any other pharmaceutically acceptable salts of hyoscyamine can be used as well for providing the dosage forms of the present invention.

In this regard, it is to be noted that any of the hyoscyamine formulations for use in the present invention may comprise hyoscyamine, a single pharmaceutically acceptable salt thereof, a combination of two or more pharmaceutically acceptable salts thereof, or a combination of hyoscyamine and one or more pharmaceutically acceptable salts thereof. Furthermore, the at least two different hyoscyamine formulations which will usually be present in the dosage forms of the present invention may comprise the same or a different form of hyoscyamine (i.e., hyoscyamine free base or a pharmaceutically acceptable salt thereof). Generally, however, these different formulations will comprise the same form of hyoscyamine. For example, the may all contain hyoscyamine sulfate.

The term "therapeutic range" as used herein and in the appended claims refers to the range of hyoscyamine plasma levels within which most patients will experience a significant therapeutic effect (including alleviation of symptoms) without an undesirable degree of adverse reactions. These plasma levels are sometimes referred to herein as "therapeutic levels".

The terms "controlled release layer" and "controlled release formulation" as used herein and in the appended claims refer to any layer and formulation that is not an immediate release layer or formulation, i.e., does not release all of the active ingredient(s) contained therein within a relatively short period (for example, not within less than 45 minutes, e.g., not within less than one hour, following the ingestion of the dosage form). Accordingly, this term is a generic term which encompasses, e.g., sustained (extended) release layers (formulations), pulsed release layers (formulations), delayed release layers (formulations), timed release layers (formulations) and the like. Preferably, the controlled release layer (formulation) will release the one or more active ingredients contained therein continuously or intermittently, for example, in approximately equal amounts per time unit, over an extended period of time such as, e.g., at least about 4 hours, at least about 5 hours, at least about 6 hours, at least about 7 hours, at least about 8 hours, at least about 10 hours, or at least about 12 hours.

In one aspect of the dosage forms of the present invention, these dosage forms are preferably capable of providing a hyoscyamine plasma concentration within the therapeutic range within a short period of time, e.g., not more than about 1 hour, preferably within not more than about 45 minutes, or within not more than about 30 minutes following the ingestion of the dosage form. This rapid release of the hyoscyamine (salt) will usually be brought about by the immediate release formulation(s) (layer(s)) of the dosage form, although already at this early point a (usually small) portion of the hyoscyamine plasma concentration may be contributed by the one or more controlled release forms (formulations) of the hyoscyamine (salt) which are also present in the dosage form.

The dosage forms of the present invention preferably are capable of providing a hyoscyamine plasma concentration within the therapeutic range for a total period of at least about 4 hours, e.g., at least about 5 hours, at least about 6 hours, at least about 7 hours, at least about 8 hours, at least about 10 hours, or at least about 12 hours. Preferably, these dosage forms are capable of providing a hyoscyamine plasma concentration within the therapeutic range in a continuous manner, i.e., without an interval or intervals within which the hyoscyamine plasma concentration falls below therapeutic levels. The latter might, for example, be the case where the hyoscyamine plasma concentration provided by the immediate release formulation has ceased to be within the therapeutic range before the controlled release formulation is capable of providing the hyoscyamine that is needed to bring the hyoscyamine plasma concentration back to therapeutic levels. In case there is such an interval of therapeutically insufficient hyoscyamine plasma concentration, this interval is preferably short, e.g., not longer than about 30 minutes, or not longer than about 15 minutes.

As will be understood by those of skill in the art, at least for a certain period of time the different hyoscyamine formulations which are present in a dosage form according to the present invention may contribute to the hyoscyamine plasma concentration simultaneously. In other words, when only two different formulations are present, there may be a period within which both the plasma concentration contributed by one formulation (e.g., an immediate release formulation) and the plasma concentration contributed by the other formulation (e.g., a controlled release formulation) by themselves would be below therapeutic levels. However, these two contributions together may still be sufficient to provide a hyoscyamine plasma concentration within the therapeutic range. Thereby the total time period over which the corresponding dosage form is capable of providing a hyoscyamine plasma concentration within the therapeutic range may be longer than the sum of the two time periods over which the two individual formulations would be capable of providing such a therapeutically effective concentration.

The period of therapeutically useful hyoscyamine plasma concentrations beyond about 2 or 3 hours will usually be mainly due to a controlled release of hyoscyamine (salt) by the one or more controlled release formulations which are preferably present in the dosage forms of the present invention. Controlled release hyoscyamine formulations which are suitable for use in the present invention may be of different types. For example, a controlled release formulation for use in the present invention may delay the release of the active ingredient(s) for a certain predetermined period of time and then release all of the active ingredients(s) substantially at once. Another non-limiting example of a controlled release formulation which is suitable for use in the present invention may release the active ingredient(s) gradually, for example, at a constant rate, at a gradually increasing rate, or at a gradually increasing and then gradually decreasing rate, etc. All of these controlled release formulations and any combinations thereof may be used in the dosage forms of the present invention.

The dosage form of the present invention, in particular, preferably a solid or semi-solid dosage form such as a tablet, capsule, suppository etc., will usually comprise hyoscyamine and/or a pharmaceutically acceptable salt thereof in a total amount of at least about 0.03 mg, e.g., at least about 0.05 mg, at least about 0.1 mg, at least about 0.2 mg, or at least about 0.25 mg. On the other hand, the total amount of hyoscyamine and/or a pharmaceutically acceptable salt thereof will usually not be higher than about 5 mg, e.g., not higher than about 4 mg, not higher than about 3 mg, or not higher than about 2 mg, again expressed as hyoscyamine free base.

The immediate release formulation which will usually be present in a dosage form according to the present invention preferably comprises hyoscyamine and/or a pharmaceutically acceptable salt thereof in an amount of at least about 0.01 mg, e.g., at least about 0.015 mg, at least about 0.02 mg, or at least about 0.025 mg, but usually in an amount which is not higher than about 2 mg, e.g., not higher than about 1 mg, or not higher than about 0.5 mg.

The one or more controlled release formulations which will usually be present in a dosage form according to the present invention preferably comprise hyoscyamine and/or a pharmaceutically acceptable salt thereof in a (total) amount of at least about 0.02 mg, e.g., at least about 0.05 mg, at least about 0.1 mg, or at least about 0.25 mg, but usually in an amount which is not higher than about 5 mg, e.g., not higher than about 4 mg, or not higher than about 3 mg, or not higher than about 2 mg, in each case expressed as hyoscyamine free base.

The dosage forms of the present invention can be liquid, solid, semisolid and semiliquid (e.g., gel-like). Non-limiting examples of liquid dosage forms include solutions, suspensions, emulsions, microemulsions and syrups. Non-limiting examples of solid dosage forms include tablets (including a tablet within a tablet, a chewable tablet etc.), capsules (e.g., a capsule containing beads or powders formulated with different materials to provide an immediate release formulation and a controlled release formulation), pills, lozenges, powders, granules, and suppositories.

In one preferred embodiment of the present invention, the dosage form is a bi-layered tablet. For example, this tablet may comprise an immediate release layer and a controlled release layer. Preferably, both of these layers contain hyoscyamine sulfate as a or the only form of hyoscyamine present therein. Also, one or both of these layers may contain one or more further active ingredients (drugs), e.g., active ingredients which enhance the therapeutic effect of the hyoscyamine and/or which may serve any other therapeutic or other purpose. A non-limiting example of such a further drug is an analgesic which may, for example be present in the immediate release layer, the controlled release layer, or both.

In another preferred embodiment, the present invention further provides a multi-layered hyoscyamine tablet which comprises at least a first, immediate release layer and a second, controlled release layer. Both layers comprise hyoscyamine and/or a pharmaceutically acceptable salt thereof, preferably hyoscyamine sulfate. The multilayered tablet may comprise one or more additional layers, for example, one, two, three, or four additional layers. These additional layers may serve various purposes. For example, they may comprise one or more additional drugs which are different from hyoscyamine and a pharmaceutically acceptable salt thereof. Of course, the first and/or second mandatory layer of the multi-layered tablet of the present invention may contain one or more additional drugs as well (e.g., an analgesic). Additionally or alternatively, the additional layer(s) may comprise additional controlled release formulations, e.g., one or more controlled release formulations which are different from the controlled release formulation(s) contained in the second layer. In this case the different controlled release layers will usually provide different release profiles (e.g., different release rates, different release periods, different release times, etc.) of the hyoscyamine (salt) and/or may contain a different form of hyoscyamine (e.g., a hyoscyamine salt in one layer and a different hyoscyamine salt in another layer)

The multi-layered tablet of the present invention will usually be made up of two or more distinct layers or discrete zones of granulation compressed together with the individual layers lying on top of one another. Layered tablets have the appearance of a sandwich because the edges of each layer or zone are exposed. These layered tablets may be prepared by compressing a granulation onto a previously compressed granulation. The operation may be repeated to produce multi-layered tablets of more than two layers. In a preferred embodiment of the multi-layered tablet of the present invention, the tablet consists of two layers.

It is to be noted that it is not necessary for the two or more individual layers of the multi-layered tablet of the present invention to lie on top of one another or otherwise be in contact with each other, and that other components can be interposed. By way of non-limiting example, a second layer (e.g., a controlled release layer) may be partially or completely surrounded by a first layer (e.g., an immediate release layer). For example, the second layer may be coated with the first layer. In the case of three layers, for example, the third layer may be partially or completely coated with the second layer, which in turn may be partially or completely coated with the first layer. Of course, these are but a few examples of the many different ways in which the various layers of the multi-layered tablet of the present invention can be arranged relative to each other. Moreover, it is to be understood that the tablets of the present invention are not limited to such multilayered tablets. By way of non-limiting example, the tablet may comprise an immediate release matrix which comprises hyoscyamine and/or a pharmaceutically acceptable salt thereof, which matrix comprises dispersed therein particles of one or more controlled release formulations which have hyoscyamine and/or a pharmaceutically acceptable salt thereof incorporated therein.

Another aspect of the present invention is formed by a liquid (including a semiliquid) dosage form, preferably a suspension, which comprises (a) hyoscyamine and/or a pharmaceutically acceptable salt thereof in an immediate release form and (b) hyoscyamine and/or a pharmaceutically acceptable salt thereof in a controlled release form. By way of non-limiting example, one component, for example, component (b) may be incorporated into a solid controlled release formulation. For example, particles of component (b) may be provided with a controlled release coating (e.g. a controlled release coating comprising an organic polymer such as, e.g., a polyacrylate). This formulation may then be comminuted, if necessary, in an appropriate manner (e.g., by milling) to form particles of a size which is small enough to be suitable for being suspended in a pharmaceutically acceptable liquid carrier. The other component, e.g., component (a), on the other hand, may be used as such (i.e., in the form of undiluted or uncompounded hyoscyamine and/or a pharmaceutically acceptable salt thereof) and/or incorporated in a solid immediate release formulation, comminuted and incorporated into the liquid carrier as well.

At least a part of component (b) may be a complex with a complexing agent. Non-limiting examples of suitable complexing agents comprise ion-exchange resins such as, e.g., (sodium) polystyrene sulfonate.

The dosage forms of the present invention can be manufactured by processes which are well known to those of skill in the art. For example, for the manufacture of bi-layered tablets, the active ingredients may be dispersed uniformly into a mixture of excipients, for example, by high shear granulation, low shear granulation, fluid bed granulation, or by blending for direct compression Excipients may include diluents, binders, disintegrants, dispersants, lubricants, glidants, stabilizers, surfactants and colorants. Diluents, also termed "fillers", are typically used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders impart cohesive qualities to a tablet formulation and are used to ensure that a tablet remains intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants facilitate tablet manufacture; non-limiting examples thereof include magnesium stearate, calcium stearate, stearic acid, glyceryl behenate, and polyethylene glycol. Disintegrants facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers inhibit or retard drug decomposition reactions, including oxidative reactions. Surfactants may be anionic, cationic, amphoteric or nonionic. If desired, the tablets may also contain minor amounts of nontoxic auxiliary substances such as pH buffering agents, preservatives, e.g., antioxidants, wetting or emulsifying agents, solubilizing agents, coating agents, flavoring agents, and the like.

Controlled release formulations may be made by choosing the right combination of excipients that slow the release of the active ingredients by coating or temporarily bonding or decreasing the solubility of the active ingredients. Examples of these excipients include cellulose ethers such as hydroxypropylmethylcellulose (e.g., METHOCEL K4M), polyvinylacetate-based excipients such as, e.g., KOLLIDON SR, and polymers and copolymers based on methacrylates and methacrylic acid such as, e.g., EUDRAGIT NE 30D.

There are several commercially available tablet presses capable of making bi-layered tablets. For example, Manesty RotaPress Diamond, a 45 station D tooling press, is capable of making bi-layered tablets described in this application. Non-limiting examples of presses for the manufacture of bi-layered tablets include Fette America Model No. PT 3090; Maneklal Global Exports (Mumbai, India) Models JD and DH series; Niro Pharma Systems, Model R292F; and Korsch AG Models XL 800 and XL 400.

DETAILED DESCRIPTION OF THE PRESENT INVENTION

The particulars shown herein are by way of example and for purposes of illustration and discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

Example 1 (Reference)

Liquid Formula

A liquid dosage form which comprises hyoscyamine sulfate is illustrated as follows:

| Ingredients | Per 5 mL | Per 425 L |
|---|---|---|
| Hyoscyamine sulfate USP | 0.125 mg | 10.635 g |
| Methyl Paraben USP | 9.0 mg | 0.765 kg |
| Propyl Paraben USP | 1.0 mg | 0.085 kg |
| Propylene Glycol USP | 259 mg | 22.016 kg |
| Saccharin Sodium USP | 3.18 mg | 0.270 kg |
| Citric Acid USP | 5.0 mg | 0.425 kg |
| Strawberry Flavor | 10 mg | 0.850 kg |
| Banana Flavor | 10 mg | 0.850 kg |
| Sorbitol Solution 70% USP | 3212.5 mg | 273.1 kg |
| Purified Water, as required to q.s. to | 5.0 mL | 425 L |

Manufacturing process for 425 L batch size: In a suitably sized stainless steel vessel, dissolve methyl paraben and propyl paraben in approximately 50 L of warm (about 45° C.), purified water. Add about half of the propylene glycol and mix for about 1 hr. In a separate 1000 L stainless steel tank equipped with a suitably sized agitator, add about 50 L of purified water. With the agitator on, add hyoscyamine sulfate, saccharin sodium and citric acid and dissolve. Add the previously prepared paraben/propylene glycol solution to the 1000 L tank. Rinse the first vessel with about 2 L of water and transfer the rinsate to the 1000 L tank. Add the remaining propylene glycol to a suitably sized stainless steel vessel and dissolve the strawberry and banana flavors. Transfer this to the 1000 L tank. Rinse the container with 2 L of purified water and transfer to the 1000 L tank. With the agitator on, add the sorbitol solution (70%) to the 1000 L tank. Stop the agitator and let the solution stand for 15 minutes. QS to 425 L with purified water. Filter product through a 1 micron filter and fill in appropriately sized containers.

Example 2 (Reference)

Suspension Formula

A suspension formula which comprises hyoscyamine sulfate is illustrated as follows:

| Ingredients | g/100 mL | kg/batch |
|---|---|---|
| Hyoscyamine Sulfate | 0.0025 | 0.0208 |
| Silica, colloidal anhydrous, NF | 1.73 | 14.417 |
| Hydroxyethylcellulose, NF | 0.05 | 0.417 |
| Sorbitol Solution 70% (non-crystallizing), NF | 34.00 | 283.333 |
| Glycerol | 14.75 | 122.917 |
| Xylitol, NF | 16.00 | 133.333 |
| Sodium Citrate, USP | 2.00 | 16.667 |
| Saccharin Sodium cryst., USP, | 0.01 | 0.083 |
| Sodium Benzoate, NF | 0.15 | 1.250 |
| Citric Acid Monohydrate, USP | 0.16 | 1.333 |
| Strawberry Flavor | 0.15 | 1.250 |
| Banana Flavor | 0.15 | 1.250 |
| Purified Water | 49.55 | 422.67 |
| Total Amount | 120.000 g | 1000.000 kg |

Manufacturing process for 1000 kg batch: In a suitably sized stainless steel vessel, dissolve saccharin sodium, sodium benzoate, citric acid, and sodium citrate in approximately 50 L of warm (about 45° C.), purified water. In another large stainless steel drum mix the silica and hyoscyamine sulfate until a uniform and consistent mixture is obtained. In a separate 1000 L stainless steel tank equipped with a suitably sized homogenizer/disperser add about 100 L of purified water. With the homogenizer on, add the silica mixture containing hyoscyamine sulfate. Add the previously prepared solution of saccharin sodium, sodium benzoate, citric acid, and sodium citrate to the 1000 L tank. Rinse the first vessel with about 2 L of water and transfer the rinsate to the 1000 L tank. Add the remaining ingredients and homogenize for 15 minutes. Filter product through a 10 micron filter and fill in appropriately sized containers.

Example 3

Bi-Layered Tablet (Direct Compression)

A bi-layered tablet in accordance with the present invention which comprises hyoscyamine sulfate is illustrated as follows:

| Ingredients | Weight/tablet (mg) | Weight/1 kg batch (in grams) |
|---|---|---|
| Layer 1 (Immediate release) | | |
| Hyoscyamine Sulfate | 0.15 | 0.3 |
| Silicified Microcrystalline Cellulose | 114.0 | 228.0 |
| Sodium Starch Glycolate | 10.0 | 20.0 |
| Magnesium Stearate | 1.0 | 2.0 |
| Layer 2 (Sustained release) | | |
| Hyoscyamine Sulfate | 0.25 | 0.50 |
| Lactose Monohydrate | 50.0 | 100.0 |
| Dicalcium Phosphate | 50.0 | 100.0 |
| KOLLIDON SR | 255.6 | 511.2 |
| Stearic Acid | 15.0 | 30.0 |
| Magnesium Stearate | 4.0 | 8.0 |
| Total | 500.0 | 1000.0 |

Manufacturing Process (a) Immediate release layer: Screen all ingredients through a USP sieve size #30. Blend hyoscyamine sulfate (0.30 gms), silicified microcrystalline cellulose (228.0 gms) and sodium starch glycolate (20.0 gms) in a twin shell blender for 20 minutes. Add magnesium stearate (2.0 gms), which acts as a lubricant, to the above blend and mix for 3 minutes.

(b) Sustained release layer: Screen all ingredients through a USP sieve size #30. Preblend a portion of the KOLLIDON SR (145 gms) and the entire hyoscyamine sulfate (0.50 gms) for 15 minutes. Add the remaining KOLLIDON SR (366.2 gms), lactose monohydrate (100.0 gms) and dicalcium phosphate (100.0 gms) to the above preblend and mix for an additional 20 minutes. Add stearic acid (30.0 gms) and magnesium stearate (8.0 gms) to the above blend and mix for three minutes.

Manufacture bi-layered tablets using a rotary bi-layer tablet press where in each tablet the immediate release layer contains 0.15 mgs of hyoscyamine sulfate and the sustained release layer contains 0.25 mgs of hyoscyamine sulfate.

Example 4

Bi-Layered Tablet (Direct Compression)

By using the process described in Example 3 above, a bi-layered tablet of the following composition may be manufactured by using direct compression:

| Ingredients | Weight/tablet (mgs) |
|---|---|
| Layer 1 (Immediate Release) | |
| Hyoscyamine Sulfate | 0.15 |
| Silicified Microcrystalline Cellulose | 133.35 |
| Sodium Starch Glycholate | 15 |
| Magnesium Stearate | 1.5 |
| Layer 2 (Sustained Release) | |
| Hyoscyamine Sulfate | 0.3 |
| Lactose Monohydrate | 88.85 |
| Dicalcium Phosphate | 88.85 |
| KOLLIDON SR | 252 |
| Stearic Acid | 15 |
| Magnesium Stearate | 5 |
| Total | 600 |

Example 5

Bi-Layered Tablet (Wet Granulation)

A bi-layered tablet in accordance with the present invention which comprises hyoscyamine sulfate in an immediate release layer and hyoscyamine sulfate in a controlled release layer is illustrated as follows:

| Ingredients | Weight/tablet (mgs) | Weight/1 kg batch (gms) |
|---|---|---|
| Layer 1 (Immediate release) | | |
| Hyoscyamine Sulfate | 0.125 | 0.179 |
| Silicified Microcrystalline Cellulose | 110.875 | 158.4 |
| Povidone | 3.0 | 4.3 |
| Croscarmellose Sodium | 10.0 | 14.3 |
| Magnesium Stearate | 1.0 | 1.4 |
| Layer 2 (Sustained release) | | |
| Hyoscyamine Sulfate | 0.25 | 0.357 |
| Microcrystalline Cellulose (PH 102) | 122.75 | 175.34 |
| Lactose Monohydrate | 100.0 | 142.9 |
| Dicalcium Phosphate | 100.0 | 142.9 |
| Povidone | 15.0 | 21.43 |
| Methocel K4M Premium | 212.0 | 302.9 |
| Stearic Acid | 20.0 | 28.6 |
| Magnesium Stearate | 5.0 | 7.14 |
| Total | 700.0 | 1000.0 |

Manufacturing Process (a) Immediate release layer: Screen all ingredients through a USP sieve size #30. Blend hyoscyamine sulfate (0.179 gms), silicified microcrystalline cellulose (158.6 gms) and croscarmellose sodium (14.3 gms) in a high shear mixer/granulator for 10 minutes. Granulate the above blend using a 30% povidone solution (4.3 gms povidone in 14.3 gms purified water). Dry the granulation until the loss on drying (LOD) is less than 2.0%. Screen the dried granulation through a USP sieve size #14. Add the screened granulation and the prescreened magnesium stearate (1.43 gms) to the above blend and mix for 3 minutes.

(b) Sustained release layer: Screen all ingredients through a USP sieve size #30. Blend the hyoscyamine sulfate (0.357 gms), microcrystalline cellulose PH 102 (175.74 gms), lactose monohydrate (142.9 gms), dicalcium phosphate (142.9 gms), METHOCEL K4M Premium (302.9 gms) and stearic acid (28.6 gms) in a high shear mixer/granulator for 10 minutes. Granulate the above blend using a 30% povidone solution (21.43 gms povidone in 71.3 gms purified water). Dry the granulation until the LOD is less than 2.0%. Screen granules through a USP sieve size #14. Add granules and the prescreened magnesium stearate (7.14 gms) to the above blend and mix for 3 minutes.

Manufacture bi-layered tablets using a rotary bi-layer tablet press where in each tablet the immediate release layer contains 0.125 mgs of hyoscyamine sulfate and the sustained release layer contains 0.25 mgs of hyoscyamine sulfate.

Example 6

Bi-Layered Tablet (Wet Granulation)

A bi-layered tablet in accordance with the present invention which comprises hyoscyamine sulfate in an immediate release layer and hyoscyamine sulfate in a controlled release layer is illustrated as follows:

| Process Steps | Ingredients | Dose(mg) | Scale-Up | |
|---|---|---|---|---|
| Sustained Release Layer | | | | |
| Wet Mix | Purified Water | 20.000 | 4.500 | kg |
| Wet Mix | Hyoscyamine Sulfate USP* | 0.290 | 65.250 | g |
| Wet Mix | Povidone K-30 USP | 9.000 | 2.025 | kg |
| Pre-blend | Calcium Phosphate Dibasic Dihydrate | 127.010 | 28.577 | kg |
| Pre-blend | PROSOLV SMCC 90 | 25.700 | 5.783 | kg |
| Pre-blend | METHOCEL K4M Premium USP | 67.500 | 15.188 | kg |
| Final blend | METHOCEL K4M Premium USP | 67.500 | 15.188 | kg |
| Lube blend | Magnesium Stearate NF | 3.000 | 0.675 | kg |
| | Layer Weight: | 300.000 | | |
| Immediate Release Layer | | | | |
| Wet Mix | Purified Water | 10.000 | 2.250 | kg |
| Wet Mix | Hyoscyamine Sulfate USP* | 0.097 | 21.825 | g |
| Wet Mix | Povidone K-30 USP | 4.500 | 1.013 | kg |
| Pre-blend | D&C Red #30 Aluminum Lake | 0.083 | 18.675 | g |
| Pre-blend | FD&C Blue #1 Aluminum Lake | 0.083 | 18.675 | g |
| Pre-blend | PROSOLV SMCC 90 | 71.782 | 16.151 | kg |
| Pre-blend | Sodium Starch Glycolate | 3.000 | 0.675 | kg |
| Final blend | D&C Red #30 Aluminum Lake | 0.083 | 18.675 | g |
| Final blend | FD&C Blue #1 Aluminum Lake | 0.083 | 18.675 | g |
| Final blend | PROSOLV SMCC 90 | 65.789 | 14.803 | kg |
| Final blend | Sodium Starch Glycolate | 3.000 | 0.675 | kg |
| Lube blend | Magnesium Stearate NF | 1.500 | 0.338 | kg |
| | Layer Weight: | 150.000 | | |
| | Totals(wt) | 450.000 | 101.253 | kg |
| | Totals (tablets) | 1 | 225.000 | |

*NOTE: 3% Excess is included for Hyoscyamine Sulfate USP

Procedure

Sustained Release Layer (Layer 1)
1. Set aside 0.5 kg of Purified Water to be used in step 4.
2. Prepare a solution using the specified scale up amounts of Hyoscyamine Sulfate, Povidone K-30, and the remaining Purified Water from step 1.
3. Blend the specified pre-blend scale up amounts of Calcium Phosphate Dibasic Dihydrate, and PROSOLV SMCC 90 with a high sheer mixer/granulator for 10 minutes.
4. With the mixer/granulator on, pump the solution prepared in step 1 into the mixer/granulator. After completion, stop the mixer/granulator and rinse the container with the Purified Water set aside in step 1. Pump the rinse water to the mixer/granulator with mixer on. Turn off mixer when completed.
5. Charge the specified pre-blend scale up amount of METHOCEL K4M premium to the mixer/granulator and mix for 1 minute.
6. Dry the granulation until the LOD is 4% or less.
7. Screen the granules through a number 14 mesh screen.
8. Screen the specified final blend scale up amount of METHOCEL K4M premium through a number 14 mesh screen.
9. Blend the screened materials from step 7 and 8 using a V-blender for 20 minutes.
10. Screen the specified lube scale up amount of Magnesium Stearate using a number 30 mesh screen.
11. Transfer the screened Magnesium Stearate to the V-blender and blend for 3 minutes. When completed discharge and set aside for step 12.
12. Manufacture bi-layered tablets using a rotary bi-layer tablet press where in each tablet layer 1 is 300.0 mgs and layer 2 is 150 mgs. Having a hardness range of 10-18 kps.

Immediate Release Layer (Layer 2)
1. Set aside 0.5 kg of Purified Water to be used in step 4.
2. Prepare a solution using the specified scale up amounts of Hyoscyamine Sulfate, Povidone K-30, and the remaining Purified Water from step 1.
3. Blend the specified pre-blend scale up amounts of D&C Red #30 Aluminum Lake, FD&C Blue #1 Aluminum Lake, Sodium Starch Glycolate, and PROSOLV SMCC 90 with a high sheer mixer/granulator for 10 minutes.
4. With the mixer/granulator on, pump the solution prepared in step 1 in to the mixer/granulator. After completion, stop the mixer/granulator and rinse the container with the Purified Water set aside in step 1. Pump the rinse water to the mixer/granulator with mixer on. Allow mixture to mix for an additional minute then turn mixer/granulator off
5. Dry the granulation until the LOD is 4% or less.
6. Screen the granules through a number 14 mesh screen.
7. Screen the specified final blend scale up amounts of D&C Red #30 Aluminum Lake, FD&C Blue #1 Aluminum Lake, Sodium Starch Glycolate, and PROSOLV SMCC 90 through a number 14 mesh screen.
8. Blend the screened materials from step 7 and 8 using a V-blender for 20 minutes.
9. Screen the specified lube scale up amount of Magnesium Stearate using a number 30 mesh screen.
10. Transfer the screened Magnesium Stearate to the V-blender and blend for 3 minutes. When completed discharge and set aside for step 12.
11. Manufacture bi-layered tablets using a rotary bi-layer tablet press where in each tablet layer 1 is 300.0 mg's and layer 2 is 150 mg's. Having a hardness range of 10-18 kp's.

Example 7 (Reference)

Extended Release Suspension

An extended release suspension which comprises hyoscyamine sulfate is illustrated as follows:

| Ingredients | Amount/5 ml |
| --- | --- |
| Hyoscyamine Sulfate Ion-Exchange Complex | Equivalent to 0.375 mgs Hyoscyamine Sulfate |
| EUDRAGIT ® L 100 | 0.2 to 2.8 grams |
| Glycerin | 315 mg |
| Polysorbate 80 | 1.5 mg |
| Carbomer (e.g., CARBOPOL ® 974) | 15 mg |
| Methyl Paraben | 9 mg |
| Propyl Paraben | 1 mg |
| Artificial Grape Flavor | 5 mg |
| FD&C Red # 40 Dye | 0.5 mg |
| Water | q.s |

Procedure:
(1) Add the appropriate amount of sodium polystyrene sulphonate USP (e.g. AMBERLITE® IRP 69) to a hyoscyamine sulfate solution.
(2) Stir the mix for 12 hrs to allow complete drug/resin complex formation.
(3) Separate and dry the insoluble drug/resin complex.
(4) Granulate the drug/resin complex with a delayed release/enteric polymer (e.g. EUDRAGIT® L 100, KOLLIDON® MAE, AQUACOAT® cPD) and dry the granules.
(5) Mill the granules, if needed.
(6) To an appropriate amount of water add the following ingredients and dissolve: Carbomer (e.g., CARBOPOL® 974), glycerin, polysorbate 80, methyl paraben, propyl paraben, artificial grape flavor, FD&C red #40 dye.
(7) Add milled granules.
(8) Add water to make up to a final volume.
(9) Agitate at suitable rate to avoid settling of the suspension and maintain a homogeneous product mixture.
(10) Fill in suitable containers ensuring that the product is homogeneous throughout the filling operation.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A pharmaceutical dosage form which comprises at least one of hyoscyamine and a pharmaceutically acceptable salt thereof, wherein the dosage form comprises two or more hyoscyamine formulations and at least one of the formulations is an immediate release formulation and at least one other one of the formulations is a controlled release formulation and the at least one immediate release formulation is capable of providing a hyoscyamine plasma concentration within a therapeutic range for a first period and the at least one controlled release formulation is capable of providing a hyoscyamine plasma concentration within a therapeutic range for a second period, and wherein the dosage form is capable of providing a hyoscyamine plasma concentration within the therapeutic range for a period which is longer than the combined first and second periods.

2. The dosage form of claim 1, wherein the dosage form comprises two hyoscyamine formulations.

3. The dosage form of claim 2, wherein the immediate release formulation is capable of providing a hyoscyamine plasma concentration within a therapeutic range within not more than about 1 hour following ingestion of the dosage form.

4. The dosage form of claim 2, wherein the dosage form is capable of providing a hyoscyamine plasma concentration within a therapeutic range within not more than about 45 minutes following ingestion of the dosage form.

5. The dosage form of claim 4, wherein the dosage form is capable of providing a hyoscyamine plasma concentration within the therapeutic range for at least about 12 hours.

6. The dosage form of claim 1, wherein the at least one controlled release formulation is capable of providing a hyoscyamine plasma concentration within the therapeutic range for at least about 7 hours.

7. The dosage form of claim 6, wherein the dosage form is capable of providing a hyoscyamine plasma concentration within the therapeutic range for at least about 10 hours.

8. The dosage form of claim 1, wherein the dosage form comprises hyoscyamine sulfate.

9. The dosage form of claim 1, wherein the dosage form comprises the at least one of hyoscyamine and a pharmaceutically acceptable salt thereof in a total amount of from about 0.03 mg to about 5 mg, expressed as hyoscyamine.

10. The dosage form of claim 2, wherein the dosage form comprises the at least one of hyoscyamine and a pharmaceutically acceptable salt thereof in a total amount of at least about 0.1 mg, expressed as hyoscyamine.

11. The dosage form of claim 10, wherein the dosage form comprises the at least one of hyoscyamine and a pharmaceutically acceptable salt thereof in a total amount of at least about 0.25 mg, expressed as hyoscyamine.

12. The dosage form of claim 10, wherein the dosage form comprises the at least one of hyoscyamine and a pharmaceutically acceptable salt thereof in a total amount of not more than about 3 mg, expressed as hyoscyamine.

13. The dosage form of claim 11, wherein the dosage form comprises the at least one of hyoscyamine and a pharmaceutically acceptable salt thereof in a total amount of not more than about 2 mg, expressed as hyoscyamine.

14. A pharmaceutical dosage form which comprises at least one of hyoscyamine and a pharmaceutically acceptable salt thereof, wherein the dosage form comprises two or more hyoscyamine formulations and at least one of the formulations is an immediate release formulation and at least one other one of the formulations is a controlled release formulation and the at least one immediate release formulation is capable of releasing the at least one of hyoscyamine and a pharmaceutically acceptable salt thereof for a first period and the at least one controlled release formulation is capable of releasing the at least one of hyoscyamine and a pharmaceutically acceptable salt thereof for a second period, and wherein the first and second periods overlap to provide a hyoscyamine plasma concentration within a therapeutic range during a period within which neither the immediate release formulation by itself nor the controlled release formulation by itself is capable of providing a hyoscyamine plasma concentration within a therapeutic range.

15. The dosage form of claim 14, wherein the overlap between the first and the second periods is not longer than about 1 hour.

16. The dosage form of claim 14, wherein the second period is longer than the first period.

17. The dosage form of claim 16, wherein the second period is at least about 4 hours long.

18. The dosage form of claim 14, wherein the dosage form comprises two hyoscyamine formulations.

19. The dosage form of claim 14, wherein the immediate release formulation is capable of providing a hyoscyamine plasma concentration within a therapeutic range within not more than about 1 hour following ingestion of the dosage form.

20. The dosage form of claim 15, wherein the dosage form is capable of providing a hyoscyamine plasma concentration within a therapeutic range within not more than about 45 minutes following ingestion of the dosage form.

21. The dosage form of claim 19, wherein the dosage form is capable of providing a hyoscyamine plasma concentration within the therapeutic range for at least about 12 hours.

22. The dosage form of claim 14, wherein the at least one controlled release formulation is capable of providing a hyoscyamine plasma concentration within the therapeutic range for at least about 7 hours.

23. The dosage form of claim 22, wherein the dosage form is capable of providing a hyoscyamine plasma concentration within the therapeutic range for at least about 10 hours.

24. The dosage form of claim 14, wherein the dosage form comprises hyoscyamine sulfate.

25. The dosage form of claim 14, wherein the dosage form comprises the at least one of hyoscyamine and a pharmaceutically acceptable salt thereof in a total amount of from about 0.03 mg to about 5 mg, expressed as hyoscyamine.

26. The dosage form of claim 25, wherein the dosage form comprises the at least one of hyoscyamine and a pharmaceutically acceptable salt thereof in a total amount of at least about 0.1 mg, expressed as hyoscyamine.

27. The dosage form of claim 14, wherein the dosage form comprises the at least one of hyoscyamine and a pharmaceutically acceptable salt thereof in a total amount of at least about 0.25 mg, expressed as hyoscyamine.

28. The dosage form of claim 27, wherein the dosage form comprises the at least one of hyoscyamine and a pharmaceutically acceptable salt thereof in a total amount of not more than about 3 mg, expressed as hyoscyamine.

29. The dosage form of claim 26, wherein the dosage form comprises the at least one of hyoscyamine and a pharmaceutically acceptable salt thereof in a total amount of not more than about 2 mg, expressed as hyoscyamine.

30. A bi-layered hyoscyamine tablet, wherein the tablet comprises a first layer and a second layer, the first layer comprising an immediate release formulation which comprises at least one of hyoscyamine and a pharmaceutically acceptable salt thereof and being capable of providing a hyoscyamine plasma concentration within a therapeutic range for a first period, and the second layer comprising a controlled release formulation which comprises at least one of hyoscyamine and a pharmaceutically acceptable salt thereof and being capable of providing a hyoscyamine plasma concentration within a therapeutic range for a second period, and wherein the tablet is capable of providing a hyoscyamine plasma concentration within the therapeutic range for a period which is longer than the combined first and second periods.

31. The bi-layered tablet of claim 30, wherein the first layer is capable of providing a hyoscyamine plasma concentration within a therapeutic range within not more than about 1 hour following ingestion of the tablet.

32. The bi-layered tablet of claim 31, wherein the second layer is capable of providing a hyoscyamine plasma concentration within the therapeutic range for a period of at least about 3 hours.

33. The bi-layered tablet of claim 30, wherein the first and second layers comprise hyoscyamine sulfate.

34. The bi-layered tablet of claim 30, wherein at least one of the first and second layers comprises a pharmaceutically active ingredient which is different from hyoscyamine and a pharmaceutically acceptable salt thereof.

35. The bi-layered tablet of claim 30, wherein the first layer comprises from about 0.01 to about 1 mg of hyoscyamine sulfate.

36. The bi-layered tablet of claim 35, wherein the second layer comprises from about 0.1 to about 5 mg of hyoscyamine sulfate.

37. The bi-layered tablet of claim 36, wherein the tablet comprises a total of from about 0.2 to about 4 mg of hyoscyamine sulfate.

38. The bi-layered tablet of claim 36, wherein the tablet is capable of providing a hyoscyamine plasma concentration within a therapeutic range for at least about 6 hours.

39. The bi-layered tablet of claim 37, wherein the tablet is capable of providing a hyoscyamine plasma concentration within a therapeutic range for at least about 10 hours.

40. The bi-layered tablet of claim 30, wherein the first layer comprises from about 0.05 mg to about 0.5 mg of hyoscyamine sulfate and is capable of providing a hyoscyamine plasma concentration within a therapeutic range within not more than about one hour following ingestion of the tablet, the second layer comprises from about 0.2 mg to about 2 mg of hyoscyamine sulfate, and the tablet is capable of providing a hyoscyamine plasma concentration with a therapeutic range for at least about 6 hours.

41. A bi-layered hyoscyamine tablet, wherein the tablet comprises a first layer and a second layer, the first layer comprising an immediate release formulation which comprises at least one of hyoscyamine and a pharmaceutically acceptable salt thereof and being capable of releasing the at least one of hyoscyamine and a pharmaceutically acceptable salt thereof for a first period, and the second layer comprising a controlled release formulation which comprises at least one of hyoscyamine and a pharmaceutically acceptable salt thereof and being capable of releasing the at least one of hyoscyamine and a pharmaceutically acceptable salt thereof for a second period, and wherein the first and second periods overlap to provide a hyoscyamine plasma concentration within a therapeutic range during a period within which neither the immediate release formulation by itself nor the controlled release formulation by itself is capable of providing a hyoscyamine plasma concentration within a therapeutic range.

42. The bi-layered tablet of claim 41, wherein the first layer is capable of providing a hyoscyamine plasma concentration within a therapeutic range within not more than about 1 hour following ingestion of the tablet.

43. The bi-layered tablet of claim 42, wherein the second layer is capable of providing a hyoscyamine plasma concentration within the therapeutic range for a period of at least about 3 hours.

44. The bi-layered tablet of claim 41, wherein the first and second layers comprise hyoscyamine sulfate.

45. The bi-layered tablet of claim 41, wherein at least one of the first and second layers comprises a pharmaceutically active ingredient which is different from hyoscyamine and a pharmaceutically acceptable salt thereof.

46. The bi-layered tablet of claim 41, wherein the first layer comprises from about 0.01 to about 1 mg of hyoscyamine sulfate.

47. The bi-layered tablet of claim 46, wherein the second layer comprises from about 0.1 to about 5 mg of hyoscyamine sulfate.

48. The bi-layered tablet of claim 47, wherein the tablet comprises a total of from about 0.2 to about 4 mg of hyoscyamine sulfate.

49. The bi-layered tablet of claim 47, wherein the tablet is capable of providing a hyoscyamine plasma concentration within a therapeutic range for at least about 6 hours.

50. The bi-layered tablet of claim 48, wherein the tablet is capable of providing a hyoscyamine plasma concentration within a therapeutic range for at least about 10 hours.

51. The bi-layered tablet of claim 41, wherein the first layer comprises from about 0.05 mg to about 0.5 mg of hyoscyamine sulfate and is capable of providing a hyoscyamine plasma concentration within a therapeutic range within not more than about one hour following ingestion of the tablet, the second layer comprises from about 0.2 mg to about 2 mg of hyoscyamine sulfate, and the tablet is capable of providing a hyoscyamine plasma concentration with a therapeutic range for at least about 6 hours.

* * * * *